United States Patent
Michard et al.

(10) Patent No.: US 8,608,683 B2
(45) Date of Patent: Dec. 17, 2013

(54) DEVICE FOR INFUSION OF AT LEAST TWO MEDICAMENTS

(75) Inventors: Frederic Michard, Gex (FR); Ulrich Pfeiffer, Munich (DE); Reinhold Knoll, Munich (DE)

(73) Assignee: UP-Med GmbH, Munich (DE)

( * ) Notice: Subject to any disclaimer, the term of this patent is extended or adjusted under 35 U.S.C. 154(b) by 552 days.

(21) Appl. No.: 12/529,493

(22) PCT Filed: Feb. 29, 2008

(86) PCT No.: PCT/EP2008/001624
§ 371 (c)(1),
(2), (4) Date: Sep. 1, 2009

(87) PCT Pub. No.: WO2008/107127
PCT Pub. Date: Sep. 12, 2008

(65) Prior Publication Data
US 2010/0137828 A1    Jun. 3, 2010

(30) Foreign Application Priority Data

Mar. 2, 2007  (DE) .......................... 10 2007 010 326

(51) Int. Cl.
*A61M 31/00*  (2006.01)

(52) U.S. Cl.
USPC .......................................... 604/67; 604/503

(58) Field of Classification Search
USPC ........ 604/500–522, 65–67, 131, 890.1–892.1
See application file for complete search history.

(56) References Cited

U.S. PATENT DOCUMENTS

| | | | |
|---|---|---|---|
| 5,002,055 A * | 3/1991 | Merki et al. .................. | 600/345 |
| 5,984,893 A | 11/1999 | Ward | |
| 2002/0156462 A1 | 10/2002 | Stultz | |
| 2004/0106953 A1* | 6/2004 | Yomtov et al. .................... | 607/3 |
| 2009/0177188 A1 | 7/2009 | Steinkogler | |

FOREIGN PATENT DOCUMENTS

| | | |
|---|---|---|
| DE | 19740387 A1 | 3/1999 |
| DE | 102005022428 A1 | 11/2006 |
| DE | 102006032875 A1 | 1/2008 |

OTHER PUBLICATIONS

International Search Report for PCT/EP2008/001624, mailed on Jul. 2, 2008.

* cited by examiner

*Primary Examiner* — Kevin C Sirmons
*Assistant Examiner* — Phillip Gray
(74) *Attorney, Agent, or Firm* — Leydig, Voit & Mayer, Ltd.

(57) ABSTRACT

A device for infusing of at least one medicament includes at least two actuators configured to cause at least two medicaments to be infused; at least one sensor configured to measure a value of at least two parameters; and a controller configured to control the at least two actuators, wherein the controller is programmed to activate the at least two actuators depending on the values of each of the at least two parameters, and wherein the controller is arranged so as to consider a dependency of the at least two medicaments.

19 Claims, 12 Drawing Sheets

DEVICE FOR INFUSION OF AT LEAST TWO MEDICAMENTS

This is a U.S. National Phase Application under 35 U.S.C. §171 of International Application No. PCT/EP2008/001624, filed on Feb. 29, 2008, which claims priority to German Patent Application No. DE 10 2007 010 326.5, filed on Mar. 2, 2007. The International Application was published in English on Sep. 12, 2008 as WO 2008/107127 under PCT article 21(2).

BACKGROUND

In patients undergoing surgery, because of vasodilation induced by anesthetic agents and hypovolemia induced by surgical bleeding, hypotension is frequently observed during the surgical procedure. Prolonged hypotension may lead to organ hypoperfusion and at the end organ failure. Prompted therapeutic intervention to normalize blood pressure is therefore expected, and is based on volume loading and/or the administration of vasoactive or/and inotropic agents.

In some instances, anesthesiologists may be interested not only in maintaining blood pressure but also in maximizing stroke volume (or increasing stroke volume until stroke volume reaches a plateau). Indeed, in patients undergoing high-risk surgery, either because of chronic disease state (e.g. hip surgery in a patient with chronic heart failure) or acute disease state (e.g. peritonitis surgery in a patient with septic shock) or/and because of the surgical procedure itself (e.g. spine hemorrhagic surgery), it has been established that maximizing stroke volume by the mean of fluid administration may decrease the incidence of postoperative complications and reduce the length of stay in the intensive care unit and in the hospital (cost saving strategy).

In patients undergoing surgery, the identification of hypotensive patients who may benefit from volume loading and of those who may benefit from vasoactive or/and inotropic agents is very difficult. For example, vasoplegic states (which may benefit from vasoactive drug administration) can be identified by evaluating systemic vascular resistances but cardiac output—a parameter necessary for the calculation of systemic vascular resistances—is usually not measured during the surgical procedure.

Hypovolemic states can be identified by assessing blood volume, or cardiac dimensions, but it is usually not the case nor possible during the surgical procedure.

In patients undergoing high-risk surgery, maximizing stroke volume implies to measure stroke volume, which is not always the case or possible and requires the use of a specific and more expensive cardiac output monitoring technology.

Even when stroke volume and cardiac output can be measured and monitored during the surgical procedure, there is no system allowing the automatic control of fluid administration and vasoactive or/and inotropic agents administration, minimizing the duration of systemic hypotension, preventing the development of organ failure, and improving the outcome of patients undergoing surgery.

SUMMARY OF THE INVENTION

Known methods for determining if a medicament should be given usually use one dedicated parameter only. The value of this parameter determines if the medicament should be given. In case it should be determined if more types of medicaments should be infused to the patient, parameters that are dedicated to these types of medicaments are measured. Based on these measurements it will be determined if these types of medicaments will be given. Within prior devices it is decided independently from the other measurements and the other medicaments if a medicament should be given.

In an embodiment, the present invention provides a device for infusing of at least one medicament that comprises at least two actuators for causing, that at least two medicaments will be infused; at least one sensor for measuring at least two parameters; a controller, that controls the actuator, the controller being programmed to activate the actuator depending on the values of the two parameters, wherein the controller is arranged for considering dependencies of medicaments. This device allows for administering medicaments considering complex systems of medicaments that depend on other medicaments.

A device for infusing is a device that administers medicine to a patient. Preferably it provides medicine from a reservoir. Preferably a device for infusing is an electrical microdosage pump or an electrical volumetric infusion pump. It is also possible that a device for infusing is based on a valve with at least two ports.

An actuator is a device that actuates an action, especially infusing and/or injecting medicaments. Preferably the actuator comprises an interface for entering data. Preferably the actuator is connected to a controller via the interface. As an actuator each device that is suited to cause that a medicament will be infused can be deployed. Preferably an electrical syringe more preferably an infusion pump for administering of fluid or red blood cells is used.

As medicament each substance that has a therapeutic effect can be used. Preferably medicaments that have an effect on cardiac output and preferably medicaments that have an effect on blood pressure are infused.

At least two medicaments are infused. Preferably a medicament is a mixture of two or more medicaments. More preferably a medicament is a single medicament. Preferably more than two medicaments are infused.

For infusing of medicaments each method can be used that administers a medicament to a patient. Preferably medicaments are administered intramuscularly, percutaneously, intradermally, hypodermically or by nebulization in the airways most preferably medicaments are infused intravenously. It is also possible to administer a medicament orally or by the respiratory system.

As sensor each measurement device can be used that is able to measure a parameter. Preferably pulse oximetry probes, electrocardiogram electrodes, blood oxygen saturation sensors, a pressure sensor connected to an arterial catheter and/or blood test are used. More preferably arterial pressure monitors, tonometers, indwelling-fiberoptic systems, continuous hematocrit monitors, continuous haemoglobin monitors, electro cardiogram monitors and pulse oximetry monitors are used.

Parameters that are used are preferably parameters that indicate the state of the cardio-circulatory system such as systolic arterial pressure, mean arterial pressure, diastolic arterial pressure, central venous pressure, pulse oximetry plethysmographic waveform variation POPV, hemoglobin concentration, hematocrit, heart rate, pulse pressure variation, systolic pressure variation, preejection period variation and central venous blood oxygen saturation or central venous blood oxygen content.

As mean arterial pressure preferably the average arterial pressure during a single cardiac circle is used. As hemoglobin preferably the concentration of the iron containing oxygen transport metalloprotein in the red blood cells is measured. For hematocrit preferably a proportion of blood volume that is occupied by red blood cells is measured. A cardiac cycle involves preferably the three major status atrial systole, ventricular systole and complete cardiac diastole. The frequency of the cardiac cycle is preferably used as heart rate. The pulse pressure is preferably the change in arterial blood pressure during a contraction of the heart. The pulse pressure variation is preferably the change in blood pressure during a single respiratory cycle. Central venous blood oxygen saturation is preferably a relative measure of the amount of oxygen that is carried central venously.

As controller each device that is able to control the actuator can be deployed. Preferably a chip or extension card, more preferably a computing device, most preferably a microcontroller or a programmable logic controller are used.

At least two parameters are measured. Preferably the parameters are measured by several sensors according to the number of parameters. For example if two parameters are measured, they are preferably measured by two or more sensors. More preferably two or more parameters are measured by one sensor. Preferably the number of measured parameters is greater than the number of infused medicaments.

The controller is arranged for considering dependencies of medicaments. Thus complex effect relationships between different medicaments are considered in infusing medicaments to a patient. Preferably the controller is arranged for determining to increase infusing a first medicament and to decrease infusing a second medicament having the same effect over a certain period of time. More preferably the controller is arranged for determining to stop infusing a second medicament until a certain time period has passed after infusing a first medicament. Preferably the controller is arranged for determining infusing two or more medicaments alternately. Preferably the controller is arranged for determining to alternate infusing two or more medicaments alternately over several periods of time. Preferably the controller is arranged for determining a rest period before infusing a medicament. Preferably the controller is arranged for determining to infuse an increasing dose of a first medicament and a decreasing dose of a second medicament and determines to increase the dose of a second medicament and to decrease the dose of the first medicament after a certain dose of the first medicament or a certain time limit has been reached. Preferably the controller is arranged for determining to infuse a second medicament in order to stop a parameter change that has been induced by a first medicament.

A medicament depends on another medicament if the other medicament influences the therapeutic effect of the medicament. Preferably two medicaments are named dependent if they are amplifying each other in increasing or decreasing a certain parameter. More preferably two medicaments are named dependent if a first medicament decreases a second medicaments effect on a certain parameter. Medicaments are named dependent even if a dependency exists only for certain parameter values or doses of medicaments infused.

Fluid, preferably crystalloid or colloid solutions, vasoactive agents and inotropic agents may increase blood pressure (SAP and MAP) and decrease HR. Fluid and vasoactive agents may decrease POPV, SPV, PPV and PEPV. Inotropic drugs may increase POPV, SPV, PPV, PEPV, HR and ScVO2. Thus inotropic drugs, fluid and vasoactive agents depend on each other. Some drugs like dopamine, dobutamine and epinephrine are vasoactive and inotropic at the same time. Some positively inotropic acting drugs like dopamine may induce vasoconstriction while others like dobutamine may induce vasodilation. These drugs could be given at the same time. Fluid decreases hemoglobin and possibly increases ScVO2. Red blood cells will increase hemoglobin and ScVO2 and decrease POPV, SPV, PPV and PEPV.

In another preferred embodiment the parameters are selected out of a group of the following: systolic arterial pressure (SAP), mean arterial pressure (MAP), pulse oximetry plethysmographic waveform variation (POPV), hemoglobin (Hb), hematocrit (ht), heart rate (HR), pulse pressure variation (PPV), systolic pressure variation (SPV), pre-ejection period variation (PEPV) and central venuous blood oxygen saturation (ScVO2).

In another preferred embodiment the medicament is selected out of a group of the following: fluid, red blood cells, vasoactive agents and positively inotropic acting agents.

As a fluid preferably red blood cells, crystalloid solution such as lactate Ringer solution, normal salin or colloid solutions such as gelatin, hydroxyethylstarch, albumin or fresh frozen plasma is used. As vasoactive agent each hormone, drug or chemical can be used which is capable to elicit vasoconstrictive or vasodilative action on the vasculature. Preferably nitroprusside, phenylephrine, ephedrine or epinephrine, more preferably dopamine or norepinephrine are used.

As inotropic agent each substance that increases the force or energy of myocardial contractions can be used. As inotropic agent preferably catecholamines or phosphodiesterase inhibitors, more preferably cardiac glycosides, most preferably calcium or calcium sensitisers are used. Preferably phosphodiesterase inhibitors or levosimendan, more preferably dobutamine, epinephrine or dopamine are used.

In another preferred embodiment the controller further comprises a maximum device, which comprises a maxima memory, that contains a value for a maximum dose of a medicament, a dose determining device for determining the dose of a medicament that is infused and a maximum stopper for stopping the infusion of a medicament in case the infused medicament reaches the maximum dose. Thus it is possible to prevent a patient from infusing too much of a medicament.

As maximum device each device can be used that is able to determine if a maximum dose or amount of a medicament is already infused and to stop the infusion of this medicament. Preferably a computing device such as a microcontroller is used.

As maxima memory every device that is able to provide a value for a maximum amount of a medicament can be used. Preferably a computer memory like a ROM, RAM or flash memory is used.

The maximum dose of a medicament is a predefined maximum dose that can be infused to a patient. The maximum dose is preferably dependent on the age, the blood pressure, the arterial pressure and/or the heart rate, more preferably on the medicaments that have been already infused to the patient, the weight and/or the gender of a patient.

The dose determining device is a device that is able to determine the dose of a medicament that is infused to a patient. Preferably the dose determining device is a measuring unit that is arranged to measure each dose of a medicament that is infused to a patient. More preferably the dose determining device is a computing device such as a microcontroller that counts doses of medicaments that are determined to be infused to the patient.

The maximum stopper is a device that is arranged for stopping the infusion of a medicament. Preferably the maximum stopper is a computer device that stops the determining of doses of a medicament that have to be infused to a patient.

In another preferred embodiment the controller further comprises an effect controlling device, that comprises an effect memory for storing a list of medicaments and corresponding expected parameter changes and a stopper for stopping the infusion of a medicament, the effect controlling device being programmed to activate the stopper in case a medicament is infused and at least one corresponding expected parameter change does not occur. Thus a patient can be protected from being treated in a way that shows no effect or probably harms an individual patient.

Preferably an alarm is given in case there is no further medicament for controlling the respective parameter and its change.

Effects that are expected are preferably parameter changes. The effect result is preferably the change of a measured parameter. Preferably an expected effect grows within a time period from infusing the medicament. More preferably an effect starts to show after a certain lag time from the infusion of the medicament. As an effect controlling device each device that is able to compare parameters to expected parameter changes and to decide if the infusion of a medicament has to be stopped can be used. Preferably a computing device is used.

As effect memory every device that is able to store effects, i.e. the history of the measured parameters can be used. Preferably a computer memory such as a RAM, ROM flash memory is used. It is also possible to use a magnetic storage such as magnetic disk or magnetic tape.

Corresponding expected parameter changes are parameter changes that will occur at the specific patient according to experience. Preferably the corresponding expected parameter changes are parameter changes that indicate a therapeutic effect of a medicament or treatment.

As stopper each device that is able to stop the infusion of a medicament can be used. Preferably a computing device especially a microcontroller is used that stops determining the infusion of a medicament to a patient. Another preferred embodiment is a device that stops the actuator from providing medicaments. Preferably this device is a computer program or a programmable logic circuit, especially a computer program, stored in an EEPROM. It is also possible to provide a valve between the actuator and the patient that prevents that a medicament will be infused to a patient that already has been provided by the actuator.

In another preferred embodiment the controller comprises a distance analyzer that determines the distance between a threshold value especially a hyper area, preferably a line for two parameters and a parameter position, the parameter position being defined by the actually measured parameters and a converting unit for converting the distance into a dose of a medicament, the controller being programmed to activate the actuator according to this dose of a medicament. Thus the dose of a medicament is determined accurately.

As distance analyzer preferably a computing device especially a microcontroller or a programmable logic controller are deployed.

A threshold, especially threshold value is preferably a predefined value for a parameter or a hyper area within the space of parameters. For two parameters the hyper area is preferably a line. Preferably a threshold is based on empirical data. Preferably a threshold separates regions of different treatment strategies. Preferably the threshold is defined by the parameter points, where a treatment should be stopped or started like dosing a medicament. Preferably a threshold value is based on data that combine the value of a parameter with a time frame showing the time elapsed from the donation of a medicament until the measured data occurred. In another preferred embodiment a threshold separates a region of parameter points where a patient is harmed. Preferably the threshold separates a region that has to be aspired. Preferably this region is a no action area. A threshold preferably varies depending on the value of certain parameters. It is possible to represent the threshold by a multi-dimensional equation. If a threshold value for two parameters is visualized this can be done e.g. as a diagram with two axes that are perpendicular, each of the axis showing the values of a specific parameter in a ascending order, the threshold value being shown as a line within the diagram. The threshold line is preferably curved more preferably there are several threshold lines for indicating whether a medicament should be infused. Preferably separate threshold hyper areas are provided for each treatment procedure. Preferably a threshold hyper area for dosing a medicament, stopping all actuators and/or giving an alarm is provided.

A parameter position is defined by the value of one or more parameters. In a diagram as described above a parameter position would be a certain point that shows the value of both measured parameters.

The distance between a parameter position and a threshold is preferably the smallest difference, especially the root mean square between the respective parameter values. Shown on a diagram the distance is preferably a line between the parameter position and the closest threshold point. If the threshold is a line, an area, a volume or the like the distance is the smallest difference between the parameter position and the threshold points being possible. If the parameters have different measurement units, they can be weighted arbitrarily for determining the distance.

Determining of the distance is preferably done by calculating the difference of the parameter values. It can be done by visualizing the data graphically and measuring the distance, also. More preferably the distance is calculated from the equation of the threshold hyper area.

As converting unit every device can be used that is able to convert the distance between the parameter position and the threshold into a dose of a medicament. Preferably a computing device especially a microcontroller or a programmable logic controller is deployed as a converting unit.

The dose of a medicament is preferably the amount of a medicament that is determined to be infused to a patient.

In another preferred embodiment the controller is a closed loop controller. Thus the effect of a medicament already being infused is considered in determining if a medicament should be infused.

The closed loop controller preferably controls the value of parameters during or/and after a medicament has been infused and uses the result to determine whether a medicament has to be infused. Dependent on the value of the parameter change the closed loop controller is arranged to determine to stop the infusion of the medicament, to increase the dose of the medicament, and/or to infuse another medicament. The controller is preferably arranged to determine to stop the infusion of one or more medicaments depending on the value of the parameters. Preferably the controller determines after a certain period of time again, if a medicament should be infused. Preferably the controller considers in determining if a medicament should be infused the total quantity of certain medicaments that have been infused. Preferably the controller considers the time of infused medicaments for decomposition. More preferably the controller stops determining to infuse a medicament after a total quantity has been reached. Preferably the controller considers the total amount of time of the therapy. More preferably the controller stops determining the medicaments after a certain duration of the therapy.

Preferably the device comprises signalling elements that show the constitution of a patient. Thus the constitution of a patient can be communicated to a doctor or a nurse conveniently. More preferably the device comprises an element that defines an alarm condition of the patient. Preferably these elements are colored areas on a monitor. More preferably these elements are optical and/or acoustic signals.

An aspect of the invention also provides a method for infusing of at least one medicament that comprises: measuring at least two parameters; causing at least two medicaments to be infused depending on the values of the two parameters, wherein dependencies of medicaments are considered.

BRIEF DESCRIPTION OF THE DRAWINGS

Preferred embodiments of the invention will now be described based on the accompanying drawings, wherein.

DETAILED DESCRIPTION

Figure 1:
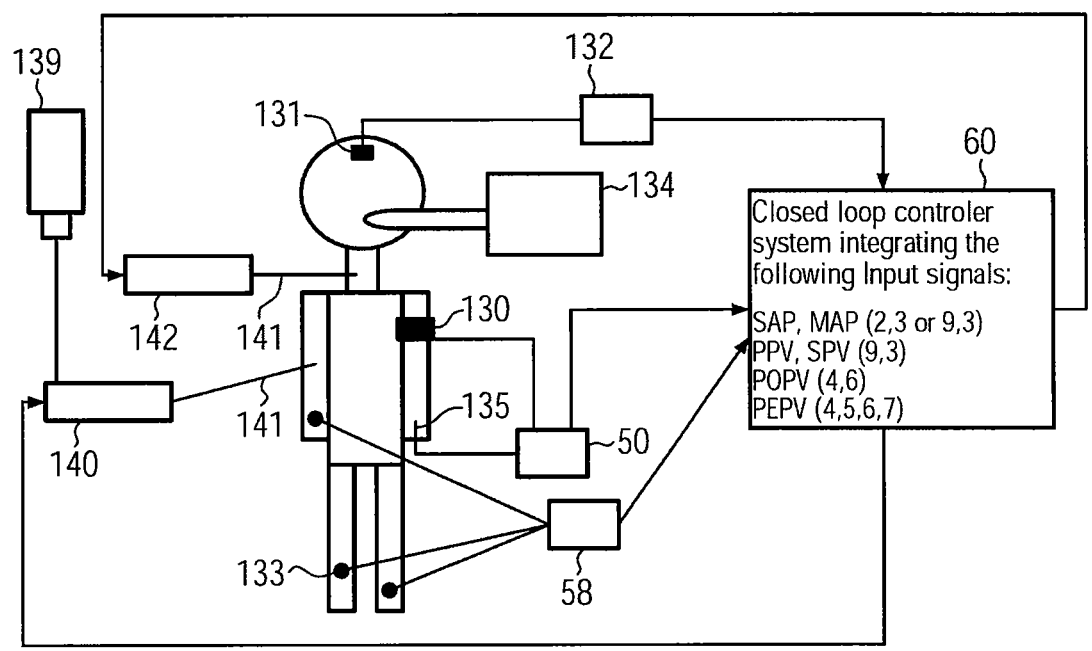
FIG. 1 shows a schematic view of a closed loop controller system according to the current invention.

FIG. 1 shows a device 1 that includes a closed loop controller system/controller 60, that gets input parameter from an arterial pressure monitor 50, that is connected to an arterial pressure cuff 130 and an arterial line 135, an electrocardiogram monitor 58 that is linked to electrocardiogram electrodes 133 and a pulse oximetry monitor 132, that is linked to a pulse oximetry probe 131. The controller 1 is connected with an infusion pump or electric syringe for vasoactive and/or inotropic agent venous infusion 142 that is linked to a venous line 141 and a perfusion pump 140 for fluid administration that is linked to another venous line and associated to a fluid bag 139. A mechanical ventilator 134 is connected to the airways of a patient.

This device 1 is preferably used for many patients undergoing surgery. In patients undergoing surgery, the most common clinical target is to maintain systolic arterial pressure (SAP) (or mean arterial pressure (MAP)) above a pre-defined threshold value SAPtv1 (or MAPtv1) and below a pre-defined threshold value SPAtv2 (or MAPtv2). With this device multiple inputs are evaluated and closed loop control for multiple outputs is generated.

The function of the device is shown in the operation diagram in FIG. 2 and described in the following.

Figure 2:
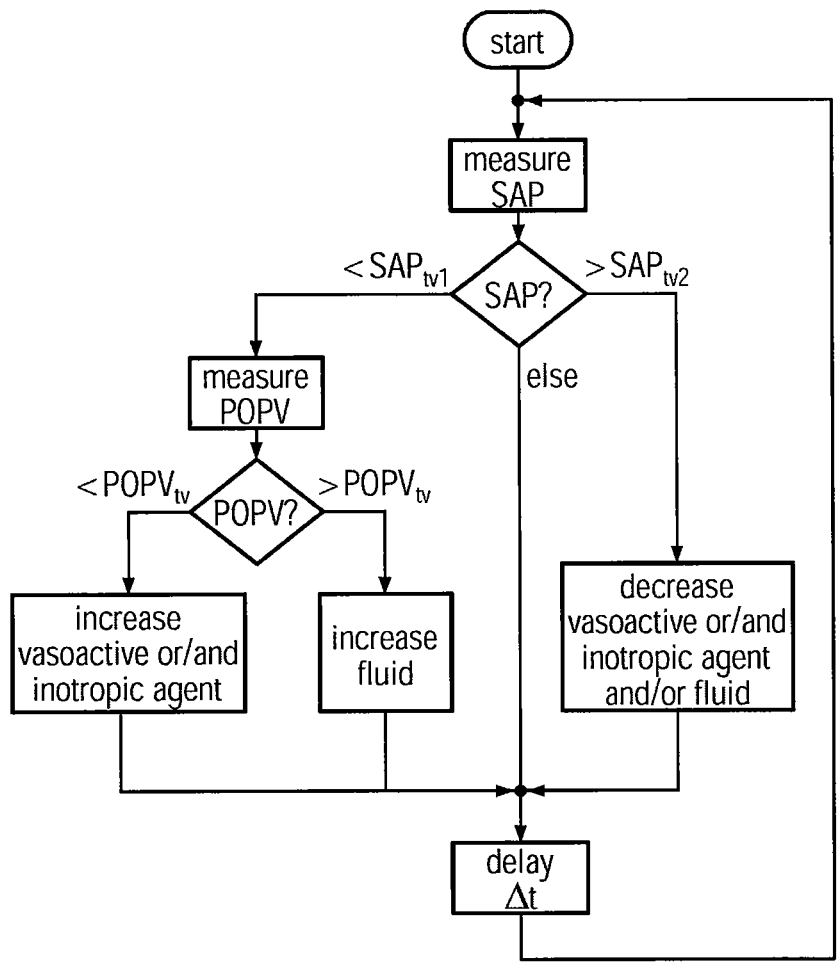
FIG. 2 shows an operation diagram of a closed loop controller according to the current invention.

FIG. 2 shows an operation diagram of an automatic closed loop controller 60 according to the current invention. The automatic controller 60 will work as follows:

First SAP (or MAP) is measured by the arterial pressure monitor.

If SAP (or MAP) is between SAPtv1 and SAPtv2 nothing is changed.

When SAP (or MAP) is above a pre-defined threshold value SAPtv2 (or MAPtv2) vasoactive or/and inotropic agent administration is decreased (or stopped) or/and fluid infusion rate is decreased.

When SAP (or MAP) is below the pre-defined threshold value SAPtv1 (or MAPtv1), the pulse oximetry plethysmographic waveform variation (POPV) (or the pre-ejection period variation PEPV, or the arterial pulse pressure variation PPV or the arterial systolic pressure variation SPV) induced by mechanical ventilation is used to select the most appropriate treatment to normalize SAP (or MAP).

POPV is derived from the analysis of the pulse oximetry plethysmographic waveform, PEPV is derived from the simultaneous analysis of the pulse oximetry plethysmographic waveform provided by the pulse oximetry monitor 54 (or the arterial pressure curve provided by the arterial pressure monitor 50) and the electrocardiogram continuous recording provided by the electrocardiogram monitor 58, and PPV or SPV are derived from the analysis of the arterial pressure curve. All these signals (POPV or PEPV or PPV or SPV) are input signals for the automatic controller 60. The automatic controller 60 is able to trigger and drive the administration of fluid and of vasoactive or/and inotropic agents in patients undergoing surgery.

As an option, the calculation of POPV (or PEPV or PPV or SPV) is refined by the additional and simultaneous recording and analyzing of a respiratory signal (e.g. an airway pressure or flow curve, or a capnographic signal, or a thoracic electrical bio-impedance signal).

In all cases, SAP (or MAP) is evaluated again after a pre-defined time frame (T) and the same automatic procedure is followed by the closed loop controller system.

If POPV (or PEPV or PPV or SPV) is above a given threshold value (POPVtv), fluid administration is started or increased automatically by an infusion pump 140 connected with and controlled by the automatic controller 60 (output signal) as shown in FIG. 1.

As an option, the blood content of hemoglobin Hb (or the blood hematocrit Hct) is also monitored continuously (or semi-continuously) and used as an additional input signal by the automatic controller 60 to determine the type of fluid infused: red blood cells or other product (e.g. crystalloid or colloid solution). When Hb (or Hct) is below a given threshold value Hbtv (or Hcttv), red blood cells are infused. When Hb (or Hct) is above the given threshold value Hbtv (or Hcttv), other type of fluids (e.g. crystalloid or colloid solution) are infused.

If POPV (or PEPV or PPV or SPV) is below a given threshold value POPVtv, a vasoactive or/and inotropic agent is given automatically by an electric syringe 142 connected with and controlled by the automatic controller (output signal) as shown in FIG. 1. For safety reasons, as soon as a vasoactive or/and inotropic agent with chronotropic properties (e.g. dopamine) is given, heart rate HR is also continuously monitored (input signal). If HR is above a given threshold value HRtv or if the patient is arrhythmic before vasoactive agent administration, vasoactive or/and inotropic agent administration is not allowed by the automatic controller system. If HR overtakes HRtv or if the patient becomes arrhythmic during vasoactive or/and inotropic agent administration, vasoactive or/and inotropic agent administration is stopped or slowed down.

Figure 3:
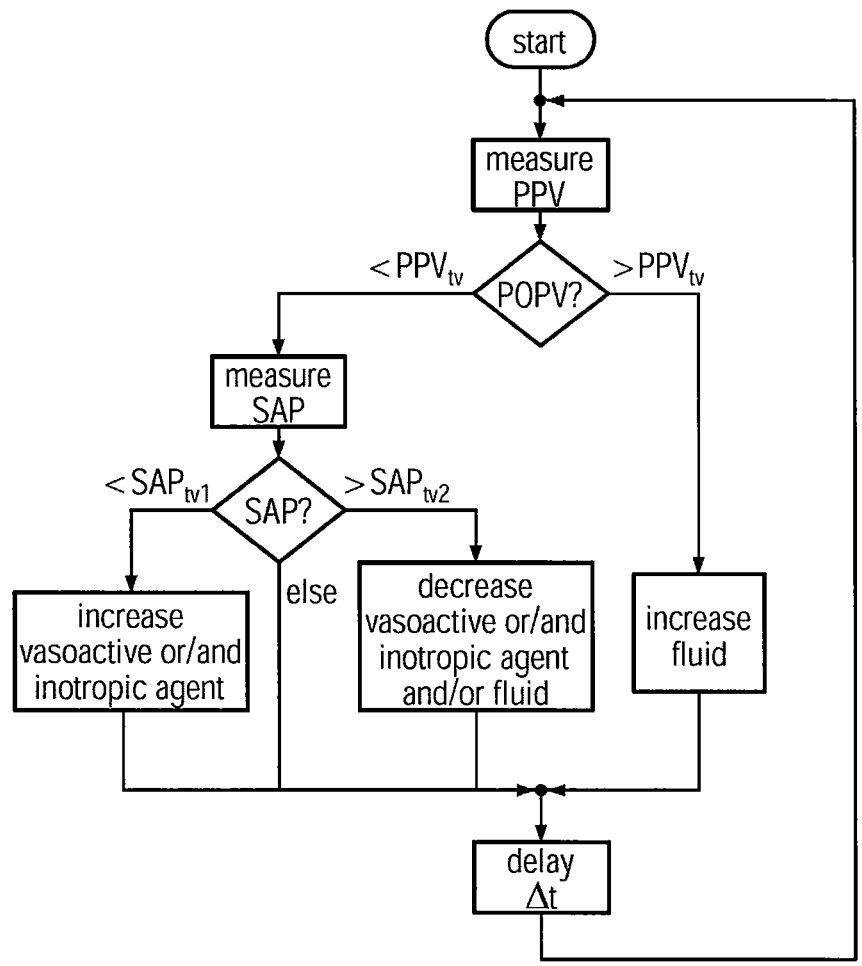
FIG. 3 shows another operation diagram of a closed loop controller according to the current invention.

FIG. 3 shows another operation diagram of a closed loop controller according to the current invention.

First PPV is measured. When PPV (or SPV or POPV or PEPV) is above a pre-defined threshold value PPVtv (or POPVtv or PEPVtv) fluid is given automatically by infusion pump 140 that is connected with and controlled by the automatic controller (output signal).

As an option, the blood content of hemoglobin Hb (or the blood hematocrit Hct) is also monitored continuously (or semi-continuously) and used as an additional input signal by the automatic controller to determine the type of fluid infused: red blood cells or other infusion (e.g. crystalloid or colloid solution). When Hb (or Ht) is below a given threshold value Hbtv (or Hcttv), red blood cells are infused. When Hb (or Hct) is above the given threshold value Hbtv (or Hcttv), other type of fluids (e.g. crystalloid or colloid solution) are infused.

If PPV (or SPV or PEPV or PPV) is below a given threshold value PPVtv, SAP is measured, and the most appropriate treatment depends on SAP (or MAP). If SAP (or MAP) is below a given threshold value SAPtv1 (or MAPtv1) a vasoactive or/and positively inotropic acting agent is given automatically by an electric syringe 142 connected with and controlled by the automatic controller (output signal). For safety reasons, as soon as a vasoactive or/and positively inotropic acting agent with chronotropic properties (e.g. dopamine) is given, heart rate HR is also continuously monitored (input signal). If HR is above a given threshold value HRtv or if the patient is arrhythmic before vasoactive or/and positively inotropic acting agent administration, vasoactive or/and positively inotropic acting agent administration is not allowed by the automatic controller system. If HR overtakes HRtv or if the patient becomes arrhythmic during vasoactive or/and positively inotropic acting agent administration, the vasoactive or/and positively inotropic acting agent administration is stopped or slowed down by the automatic controller system.

If SAP (or MAP) is above a pre-defined threshold value SAPtv2 (or MAPtv2), vasoactive or/and positively inotropic acting agent administration is decreased (or stopped) or/and fluid infusion rate is decreased.

If SAP (or MAP) is between SAPtv1 and SAPtv2 nothing is changed. In all cases, PPV (or SPV or POPV or PEPV) is evaluated again after a pre-defined time frame (T) and the same automatic procedure is followed by the closed loop controller system.

In some patients undergoing surgery (mainly high-risk surgery) the clinical target may be not only to maintain blood pressure within a predefined range (e.g. between SAPtv1 and SAPtv2 as described above) but also to maximize stroke volume (or increase stroke volume until it reaches a plateau value) by the mean of fluid loading.

When cardiac output and stroke volume are not measured or monitored, it is possible to replace the clinical target "maximizing stroke volume" by the clinical target "minimizing PPV" (or SPV or POPV or PEPV as input signals (FIG. 1)). When PPV (or SPV or POV or PEPV) is low, mechanical inspiration-induced changes in cardiac preload do not induce significant variation in stroke volume, that is that the patient is not sensitive to changes in cardiac preload.

In contrast, if PPV (or SPV or POV or PEPV) is high, it means that mechanical inspiration-induced changes in cardiac preload induces significant variations in stroke volume, that is that the patient is sensitive to changes in cardiac preload, and hence could increase more his stroke volume in response to further fluid administration. Therefore, PPV (or SPV or POPV or PEPV) can be used as a tool to know if fluid administration would be able or not to further increase stroke volume. If not, the patient has reached the maximum stroke volume he is able to achieve by receiving fluid. Therefore, when "minimizing PPV" (as a surrogate for "maximizing stroke volume") is chosen as the clinical target during the surgical procedure, the algorithm, that is shown in FIG. 3 can be applied by the closed loop controller system, too.

Figure 4:
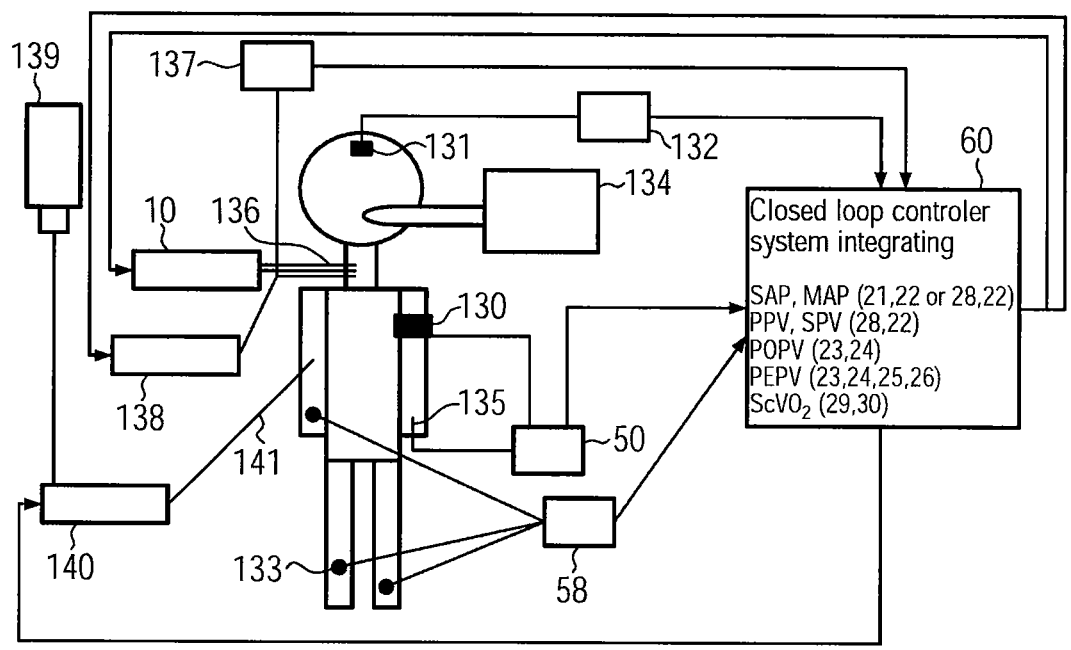
FIG. 4 shows a schematic view of another closed loop controller system according to the current invention.

FIG. 4 shows another embodiment of a device 1 with a closed loop controller system 60. This device 1 comprises four additional features compared to the device 1 shown in FIG. 1. Here the closed loop controller system 60 gets input from a central venous blood oxygen saturation monitor 137 that is linked to a central venous line 136. The closed loop controller system 60 is connected to an electric syringe for vasoactive agent venous infusion 10 and an electric syringe for a positively inotropic acting agent venous infusion 138.

This embodiment is applied, when PPV has been minimized by the use of fluid administration (meaning that stroke volume has reached a plateau value or has been "maximized" by fluid infusion), as described in the previous algorithm. In this case the anesthesiologist is interested in increasing the stroke volume by using positively inotropic acting agents. In this case, the clinical target is to reach a pre-defined threshold value of oxygen delivery or central venous blood oxygen saturation (ScVO2) or central venous oxygen content (CvO2). Therefore ScVO2 or CvO2 are monitored continuously or semi-continuously. ScvO2 or CvO2 are used as an additional signal input for a closed loop automatic controller system.

Figure 5:
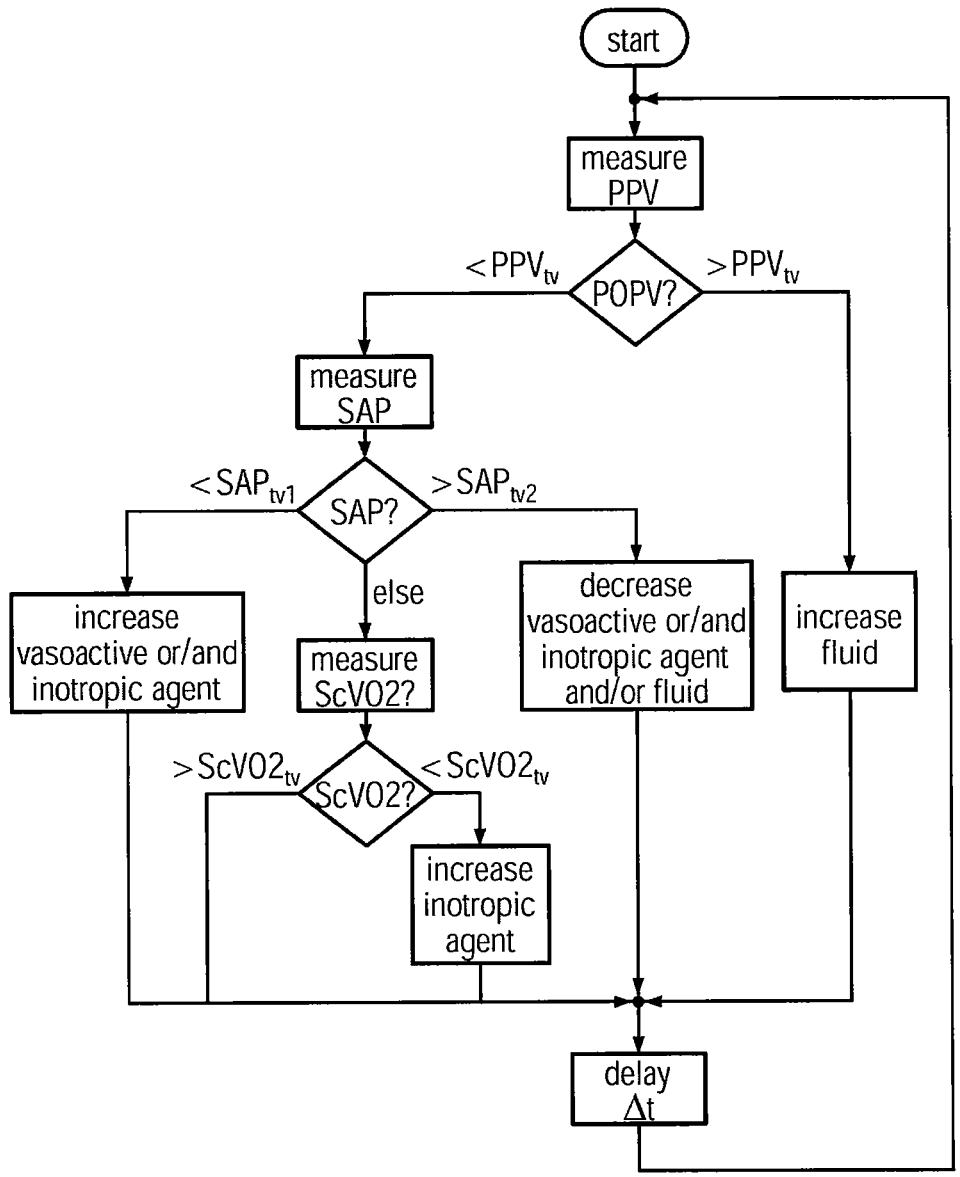
FIG. 5 shows another operation diagram of a closed loop controller according to the current invention.

The function of this system is described by means of the diagram shown in FIG. 5. FIG. 5 shows an operation diagram of a closed loop controller according to the current invention. This operation diagram shows a controlling loop of the device 1 similar to the controlling loop shown in FIG. 3. Compared to FIG. 3 FIG. 5 shows an additional loop implemented in the algorithm shown in FIG. 3. This algorithm is used with a system shown in FIG. 4.

As soon as the targeted PPV (or SPV or POPV or PEPV) and SAP (or MAP) values have been reached, according to the previous algorithm presented in FIG. 3, ScvO2 or CvO2 measurements are analyzed by the closed loop controller system, which is added to the algorithm in FIG. 5.

If ScVO2 or CvO2 is below a pre-defined threshold value (ScvO2tv or CvO2tv), positively inotropic acting drug infusion is started or increased (output signal). For safety reasons, as soon as a positively inotropic acting agent with chronotropic properties (e.g. dobutamine or epinephrine) is given, heart rate HR is also continuously monitored (input signal). If HR is above a given threshold value HRtv or if the patient is arrhythmic before inotropic agent administration, positively inotropic acting agent administration is not allowed by the automatic controller system (output signal). If HR overtakes HRtv or if the patient becomes arrhythmic during positively inotropic acting agent administration, the positively inotropic acting agent administration is stopped or slowed down by the automatic controller (output signal).

If ScvO2 or CvO2 is above the pre-defined threshold value ScvO2tv or CvO2tv, nothing is changed. In all cases, PPV (or SPV or POPV or PEPV) is evaluated again after a pre-defined time frame (T) and the same automatic procedure is followed by the closed loop controller system.

Figure 6:
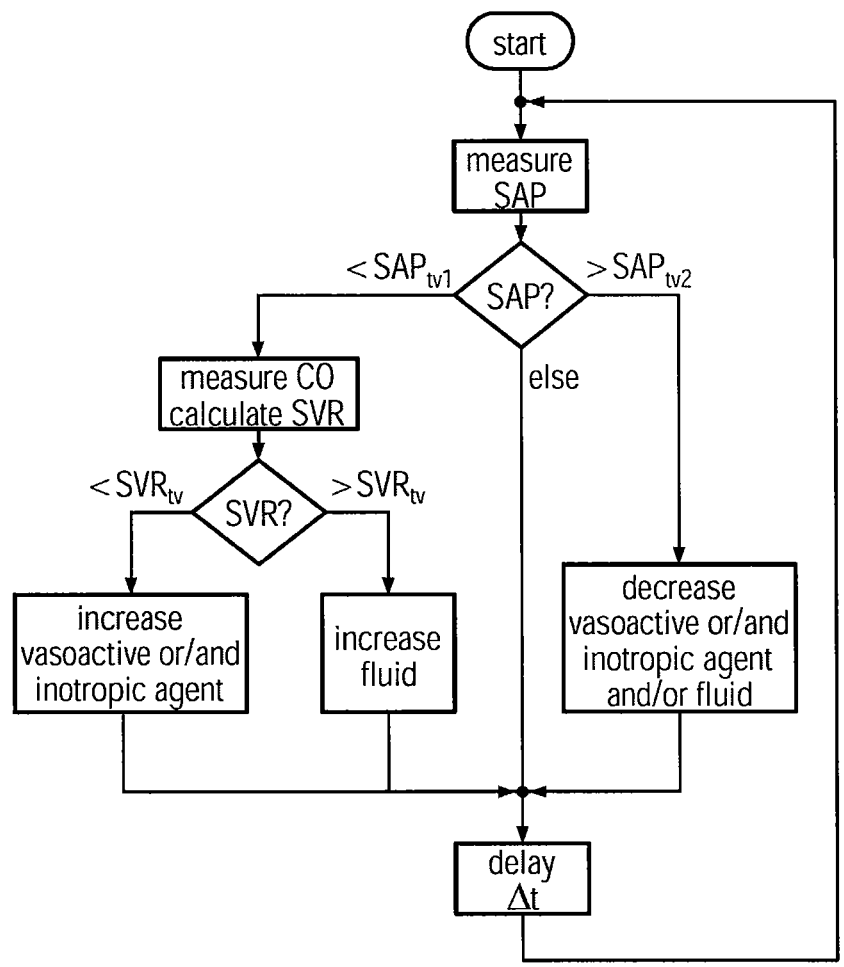
FIG. 6 shows another operation diagram of a closed loop controller according to the current invention.

FIG. 6 shows another operation diagram of a closed loop controller according to the current invention.

First SAP (or MAP) is measured. When SAP (or MAP) is below the pre-defined threshold value SAPtv1 (or MAPtv1), the systemic vascular resistance SVR is used to select the most appropriate treatment to normalize SAP (or MAP). SVR is derived from the simultaneous measurement of MAP and CO as follows: SVR=f (MAP, CO). As an option, the calculation of SVR is refined by the additional and simultaneous recording and analysis of the central venous pressure CVP as follows: SVR=f (MAP, CVP, CO).

In this case the automatic controller 60 will work as follows: If SVR is above a given threshold value (SVRtv), fluid infusion is increased automatically by an infusion pump 140 connected with and controlled by the automatic controller 60 (output signal). As an option, the blood content of hemoglobin Hb (or the blood hematocrit Ht) is also monitored continuously (or semi-continuously) and used as an additional input signal by the automatic controller to determine the type of fluid to be infused: red blood cells or other type of fluid (e.g. crystalloid or colloid solution). When Hb (or Hct) is below a given threshold value Hbtv (or Hcttv), red blood cells are infused. When Hb (or Hct) is above the given threshold value Hbtv (or Hcttv), other type of fluids (e.g. crystalloid or colloid solution) are infused.

If SVR is below a given threshold value SVRtv, a vasoactive agent is given automatically by an electric syringe 142 connected with and controlled by the automatic controller (output signal). For safety reasons, as soon as a vasoactive agent with chronotropic properties (e.g. dopamine) is given, heart rate HR is also continuously monitored (input signal). If HR is above a given threshold value HRtv or if the patient is arrhythmic before vasoactive agent administration, vasoactive agent administration is not allowed by the automatic controller system. If HR overtakes HRtv or if the patient becomes arrhythmic during vasoactive agent administration, vasoactive agent administration is stopped or slowed down.

If SAP (or MAP) is above a pre-defined threshold value SAPtv2 (or MAPtv2), vasoactive agent administration is decreased (or stopped) or/and fluid infusion rate is decreased.

If SAP (or MAP) is between SAPtv1 and SAPtv2 nothing is changed. SAP (or MAP) is evaluated again after a pre-defined time frame ($\Delta T$) and the same automatic procedure is followed by the closed loop controller system.

This algorithm is used by the automatic controller system to trigger and to drive fluid and vasoactive drugs administration, when stroke volume SV or cardiac output CO are measured and monitored during the surgical procedure (e.g. by pulse contour analysis or esophageal Doppler or the partial carbon dioxide $CO_2$ rebreathing method or electrical bioimpedance method).

This algorithm is used if the clinical target is to maintain systolic arterial pressure (SAP) (or mean arterial pressure MAP) above a pre-defined threshold value SAPtv1 (or MAPtv1) and below a pre-defined threshold value SAPtv2 (or MAPtv2).

An alternative to the use of SVR as an input signal to trigger and drive the administration of fluid and of vasoactive agents is to use POPV or PEPV or PPV or SPV, as described in the description of FIG. 2. If SV is measured and monitored beat-by-beat during the surgical procedure, the stroke volume variation SVV can also be used instead of POPV or PEPV or PPV or SPV according to the algorithm described in the description of FIG. 2.

Alternatively SV (or CO) measured continuously can be used as input signal of the controller and the controller can deliver fluid automatically until SV reaches a plateau, i.e. SV does not increase significantly (e.g. by more than 10%) during fluid administration (e.g. during the infusion of 250 mL of a colloid solution over a period of 2 minutes), as well as each time SV drops significantly (e.g. by at least 10%) during the surgical procedure. As an option, instead of a CO monitor (measuring CO accurately), a monitor able to track changes in CO (i.e. able to detect a decrease or an increase in CO) can be used. As another option, the blood content of hemoglobin Hb (or the blood hematocrit Hct) can also be monitored continuously (or semi-continuously) and be used as an additional input signal by the automatic controller to determine the type of fluid infused: red blood cells or other product (e.g. crystalloid or colloid solution). When Hb (or Ht) is below a given threshold value Hbtv (or Hcttv), red blood cells are infused. When Hb (or Ht) is above the given threshold value Hbtv (or Hcttv), other type of fluids (e.g. crystalloid or colloid solution) are infused.

An alternative to the usage of SV as an input signal is to use POPV, PEPV, PPV or SPV as described in the description of FIG. 3. If SV is measured and monitored beat-by-beat during the surgical procedure, the stroke volume variation SVV can also be used instead of POPV, PEPV, PPV or SPV according to the algorithm described in the description of FIG. 3.

This algorithm can be used for "maximizing stroke volume", particularly in patients undergoing high-risk surgery.

If arterial blood oxygen saturation SaO2 and Hb are measured and monitored, DO2 can be calculated: DO2=f (CO, SaO2, Hb). If the patient is equipped with a central venous line, ScVO2 can be measured. In this context, DO2 or ScvO2 or CvO2 can be used as additional signal input for the closed loop automatic controller system as follows:

As soon as SV has reached a plateau with fluid, DO2 (or ScVO2 or CvO2) values are analyzed by the closed loop controller system.

If DO2 is below a pre-defined threshold value (DO2tv), inotropic drug infusion is started or increased (output signal). For safety reasons, as soon as an inotropic agent with chronotropic properties (e.g. dobutamine or epinephrine) is given, heart rate HR is also continuously monitored (input signal). If HR is above a given threshold value HRtv or if the patient is arrhythmic before inotropic agent administration, positively inotropic acting agent administration is not allowed by the automatic controller system (output signal). If HR overtakes HRtv or if the patient becomes arrhythmic during positively inotropic acting agent administration, the positively inotropic acting agent administration is stopped or slowed down by the automatic controller (output signal).

If DO2 (or ScvO2 or CvO2) is above the pre-defined threshold value DO2tv, nothing is changed.

In all cases, DO2 (or ScvO2 or CvO2) is evaluated again after a pre-defined time frame (T) and the same automatic procedure is followed by the closed loop controller system.

This algorithm is used, when SV has been maximized by the use of fluid administration (or has reached a plateau value) and the anesthesiologist is interested in increasing more SV by using positively inotropic acting agents. In this case, the clinical target is to reach a pre-defined threshold value of oxygen delivery (DO2) or central venous blood oxygen saturation (ScVO2).

Figure 7:
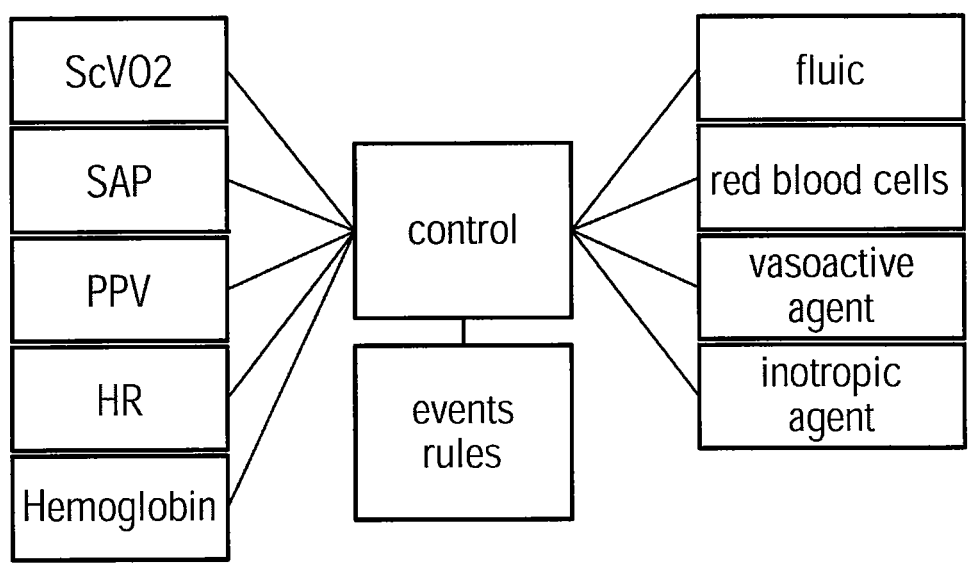
FIG. 7 shows parameters, which are input parameters for a controller/control according to the invention and medicaments, which are infused by an actuator in case the controller activates the actuator to do so.

FIG. 7 shows parameters, which are input parameters for a controller/control according to the invention and medicaments, which are infused by an actuator in case the controller activates the actuator to do so. The parameters are ScVO2, SAP, PPV, HR and hemoglobin, the medicaments are fluid, red blood cells, vasoactive agent and positively inotropic acting agent. The controller uses events and rules to determine which medicament has to be dispensed based on the measured parameters.

Figure 8:
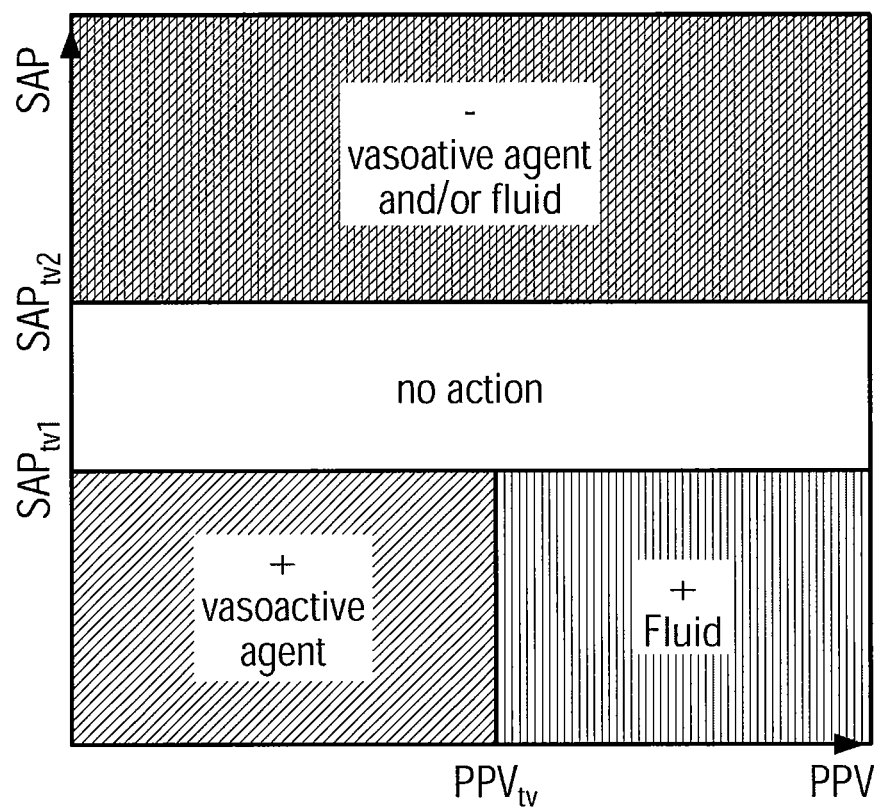
FIG. 8 shows a diagram that is used by a controller to determine whether a medicament has to be infused.
Figure 9:
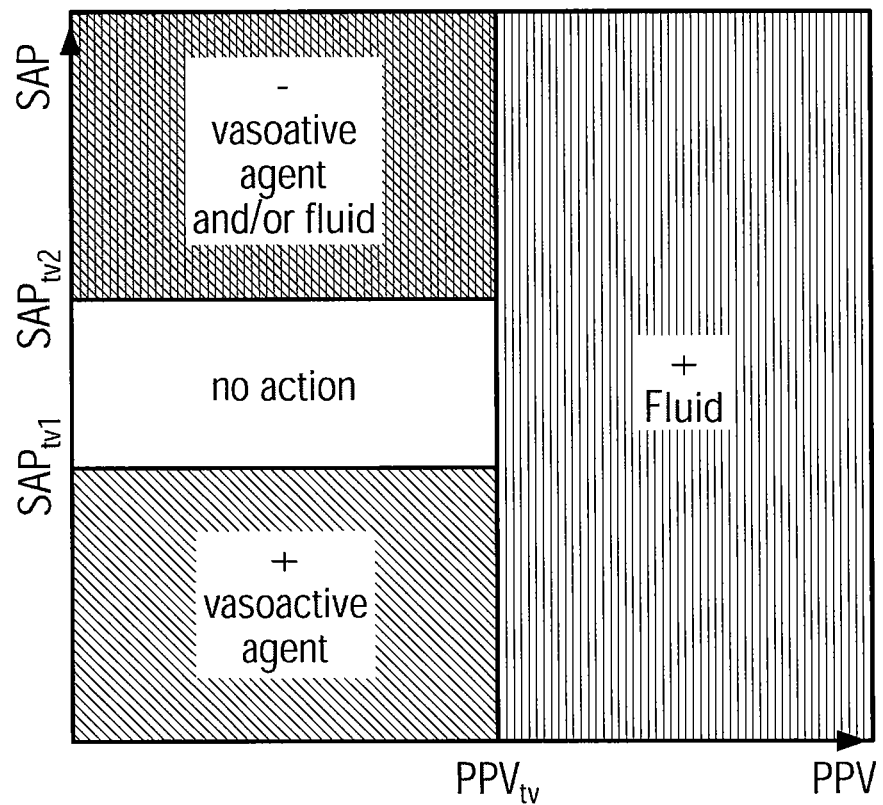
FIG. 9 shows another diagram that is used by a controller to determine whether a medicament has to be infused.
Figure 10:
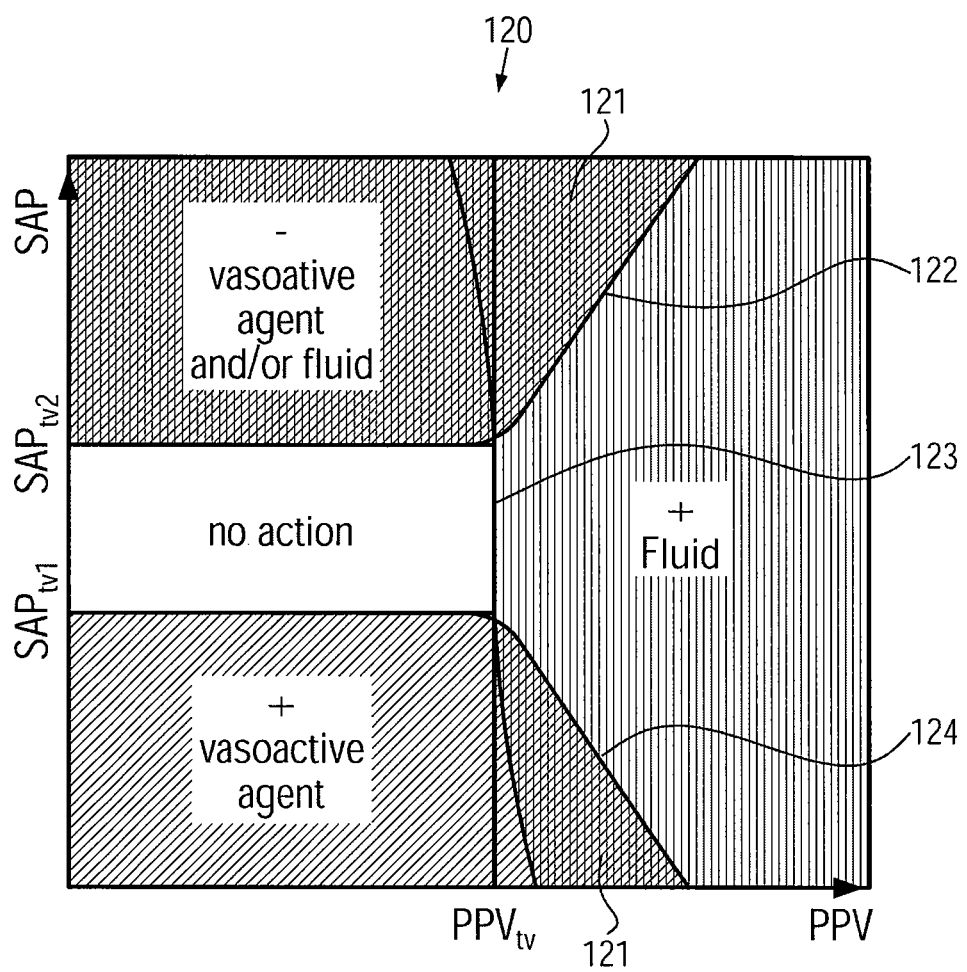
FIG. 10 shows another diagram that is used by a controller to determine whether a medicament has to be infused.

FIGS. 8, 9 and 10 show diagrams that are used by a controller to determine, whether a medicament has to be infused. Besides a decision tree algorithm with boolean logic, characteristic diagrams could be used. Thereby several actions are assigned to every point of the multidimensional space of measured or calculated parameters. Mathematically this could be described by m equations (m=number of actions)

with dimension of n (n=number of parameters). The treatment of FIG. 8 is similar to FIG. 6 and FIG. 9 is similar to FIG. 5.

FIG. 8 shows a diagram with two perpendicular axes. These axes represent a value of PPV and a value of SAP and span a vector space. In this vector space four areas are shown.

In the area representing low values of SAP, or values of SAP that are below a value of SAPtv1, two areas are shown depending on the value of PPV. For values that are below a threshold value of PPVtv an area is spanned that instructs to increase vasoactive agent. For values that are above PPVtv an area is spanned that instructs to increase fluid.

The area that represents values of SAP that are between the threshold value SAPtv1 and SAPtv2 instructs to conduct no action. This applies to all values of PPV.

The area that represents values of SAP that are above SAPtv2 instructs to reduce vasoactive agent and/or fluid. This applies to all values of PPV.

FIG. 9 is similar to FIG. 8 for values of PPV that are below PPVtv. For values of PPV that are above PPVtv an area is shown that instructs to increase fluid. This applies to all values of SAP.

FIG. 10 shows a diagram 120 with curved threshold lines 122, 123, 124. This diagram 120 shows areas 121 that indicate the infusion of two medicaments. These areas 121 are generated by two action areas that overlap and instruct to increase or decrease the infusion of one or more medicaments. Treatments that are impossible to be induced with a decision tree could be realized with characteristic diagrams. E.g. curvilinear regions like in FIG. 10.

The map is defined with an area of no action. This is realized by two separate, non-overlapping maps for dosage increase and dosage decrease for a vasoactive agent. This is due to the fact, that it is not necessary to force the patient's physiological functions to a certain physiological point but to target a certain range.

The influence of the effects of various treatments (interventions) on the indication or contra-indication of another treatment can be incorporated. E.g. the dosage of vasoactive agents may have an influence on the PPV, PEPV, POPV, SPV or SVV. Therefore in FIG. 10 fluid dosage may be decreased in case of vasoactive agents are given, see area 121. Also there is an advantage in gradually changing actions and overlapping regions.

Preferably the actions are of a differential type like increase/decrease dosage of agents instead of absolute dosage rates. Thereby with the patients physiological reaction a control loop is established.

Figure 11:
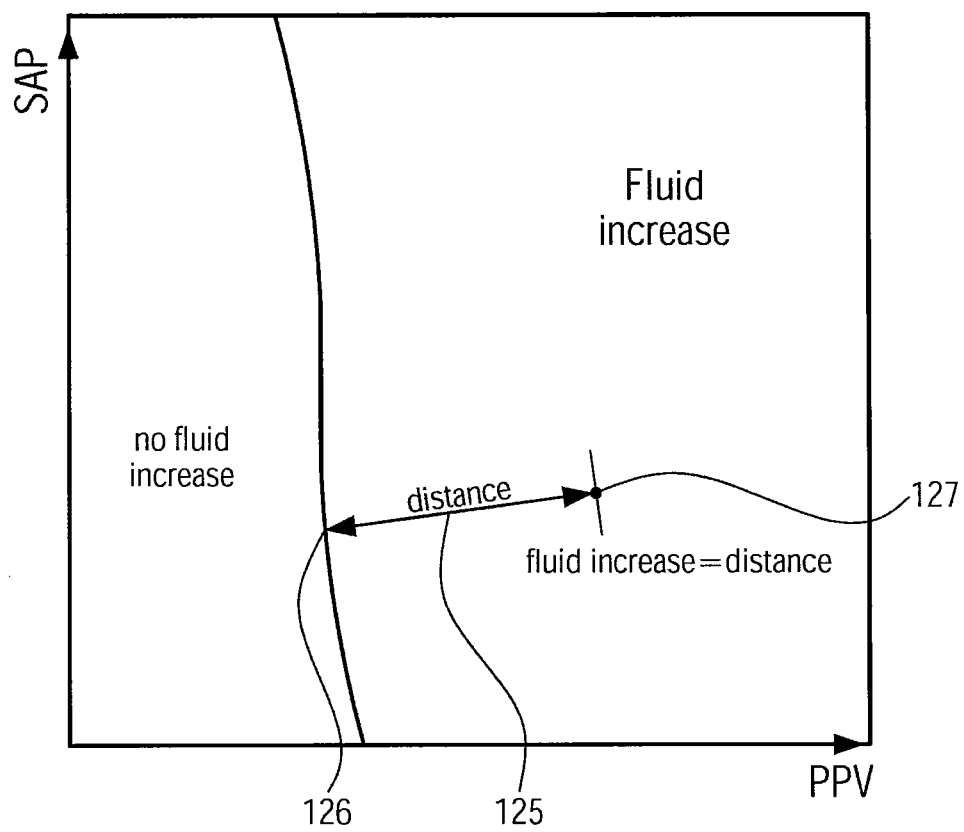
FIG. 11 shows a diagram, that is used by a controller to determine how much of a medicament has to be infused.

FIG. 11 shows a diagram that is used by a controller to determine how much of a medicament has to be infused. In FIG. 11 a boundary line and a parameter position are shown. The parameter position is defined by the measured SAP and PPV. The distance between the boundary line and the current position is used to calculate the dosage amount. The distance is the smallest possible difference between the measured values and the threshold values. If several values are measured and several threshold values are given, mathematically distance functions such as the discrete metric or the Euclidean metric are used. If more than two parameters are used a hyper area within the n-dimensional space can be used instead of the boundary line. Further the dosage amount is limited to a minimum and maximum dosage value.

This method could be applied also by using another volume responsiveness parameter (like SPV, PEPV, POPV, SVV) or another pressure related parameter (like MAP).

The described controllers act similar to an integral controller. In some cases it could be more appropriate to adapt this method similarly to a proportional controller type. This could be done e.g. by assigning absolute dosage rates within the characteristic diagrams.

Preferably some advanced control procedures are added to the described controllers. For any agent to be applied an allowable maximum dose is checked. The device should only apply a predefined amount of agents and stop the procedure if the monitored parameters will not move into the expected targeted range. This is due the fact, that the parameters are often influenced indirectly with adverse effects. The physiologic knowledge is based on statistical/empirical observations. An individual patient could react to the treatment in a different way because of a physiologic anomaly or illness.

Figure 12:
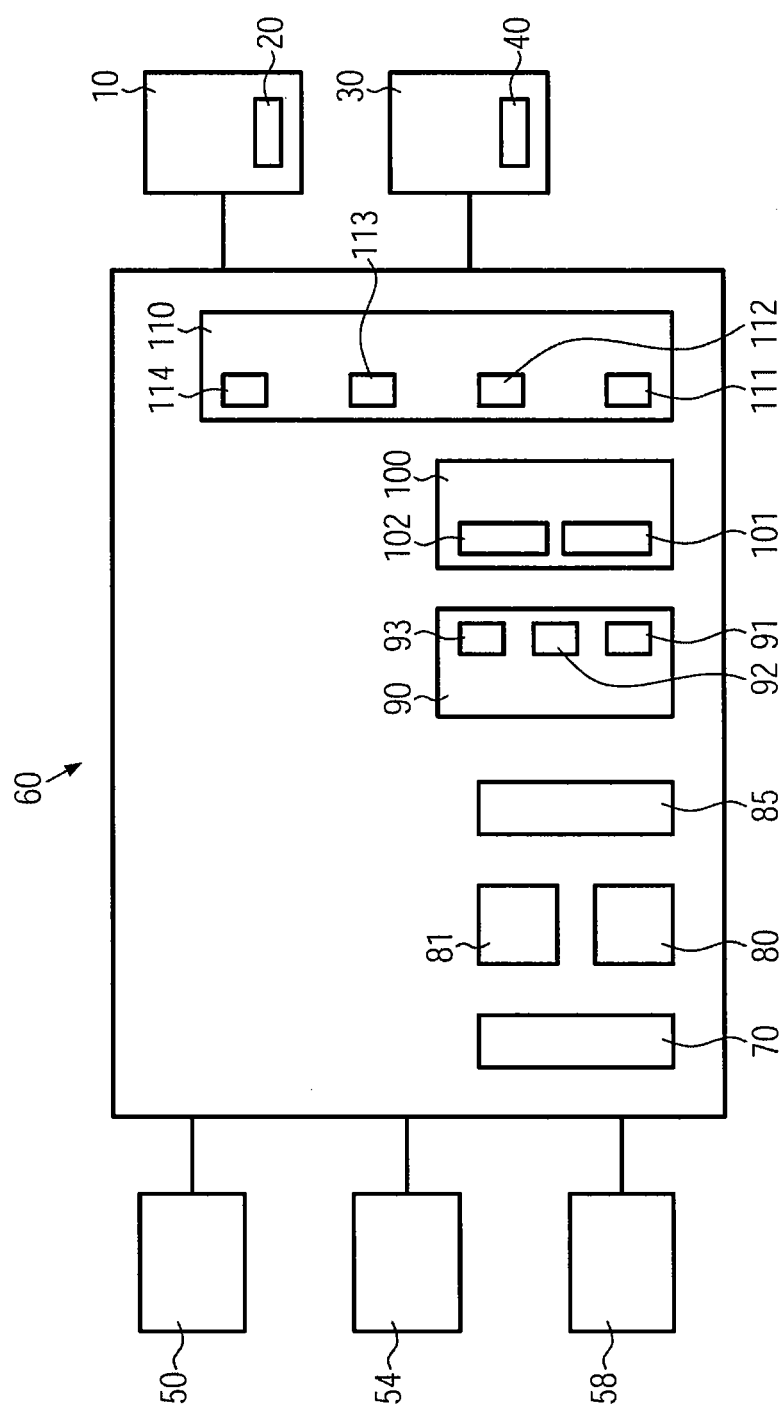
FIG. 12 shows a schematic view of an embodiment of a device for infusing of two different medicaments.

FIG. 12 shows a schematic view of an embodiment of a device for infusing of two different medicaments. The device 1 comprises a first electric syringe or infusion pump 10 with a vasoactive agent 20 and a second electric syringe or infusion pump 30 with fluid 40 that are connected to a controller 60. The controller 60 comprises a flash memory 70, a microcontroller 80 that is connected to a converting unit 81, a quartz clock or internal device of a microcontroller 85, a maximum device 90 that contains a flash memory 91, a dose determining device 92 and a maximum stopper 93, an effect controlling device 100 that contains a flash memory 101 and a stopper 102, a parameter device 110 with a list memory/flash memory 111, a detecting device or in-line flow sensor 112, a decision device or microcontroller 113 and a trigger 114. The controller 60 is connected to an arterial pressure monitor 50, a pulse oximetry monitor 54 and an electrocardiogram monitor 58.

The device 1 infuses a vasoactive agent 20 or fluid 40 depending on measured first and second parameters measured by the arterial pressure monitor 50, the pulse oximetry monitor 54 and/or the electrocardiogram monitor 58. The decision to infuse a vasoactive agent 20 or fluid 40 is based on a diagram 120 (FIG. 10) stored in a flash memory 70, which shows for every combination of the first and the second parameter, which medicament 20, 40 has to be infused. There are areas 121 in the diagram that plan to infuse fluid as well as vasoactive agent. The threshold lines 122, 123 and 124 are curved in order to adapt the threshold to the requirements. There is a "no action" area also that indicates to infuse no medicament 20, 40.

Based on FIG. 11 the microcontroller or distance analyzer 80 connected to the converting unit 81 for converting distances into values calculates the dose of a medicament to be infused.

The quartz clock 85 provides time slices inducing the device to accomplish the respective calculations regarding infusing of medicaments described above. Here the quartz clock also induces the arterial pressure monitor 50, the pulse oximetry monitor 54 and/or the electrocardiogram monitor 58 to conduct measurements, thus measurements are not conducted continuously.

The maximum device 90 is arranged for determining a maximum value and stopping the infusion of medicaments in case a maximum value is achieved. The flash memory 91 stores a list of medicaments and the maximum dose allowable for an individual patient, the dose determining device 92 determines how much medicaments are induced to the patients and the maximum stopper 93 stops infusing of medicaments to the patient by stopping the controller 60 to determine the first electric syringe 10 and second electric syringe 30 to induce a medicament.

The effect controlling device 100 controls if an expected effect occurs. If that is not the case the effect control stops infusing the respective medicament. The flash memory 101 contains a list of expected effects for a specific patient. The stopper 102, stops infusing of medicaments to the patient by stopping the controller 60 to determine the first electric syringe 10 and second electric syringe 30 to induce a medicament.

The parameter device 110 decides whether certain parameters, e.g. the heart rate should be measured and triggers the pulse oximetry monitor 54 to do so. The list memory 111 contains a list of medicaments and parameter conditions with the information, if the heart rate should be measured if these medicaments are infused and/or parameter are measured. The detecting device 112 detects, if a condition occurred that is indicated by the list for measuring the heart rate. The decision device 113 decides whether the heart rate should be measured and the trigger 114 triggers the pulse oximetry monitor 54 or the electrocardiogram monitor 58 to measure the heart rate.

REFERENCE SIGNS

1 Device
10 Electric syringe for vasoactive agent venous infusion
20 Vasoactive Agent
30 Second Electric Syringe
40 Fluid
50 Arterial Pressure Monitor
54 Pulse Oximetry Monitor
58 Electrocardiogram Monitor
60 Controller
70 Diagram Memory/Flash Memory
80 Distance Analyzer/Microcontroller
81 Converting Unit
85 Timing Device/Quartz Clock
90 Maximum Device
91 Maxima Memory/Flash Memory
92 Dose determining device
93 Maximum Stopper
100 Effect Controlling Device
101 Effect Memory/Flash Memory
102 Stopper
110 Parameter Device
111 List Memory
112 Detecting Device
113 Decision Device
114 Trigger
120 Diagram
121 Area
122 Threshold Line
123 Threshold Line
124 Threshold Line
125 Distance
126 Threshold Value
127 Parameter Position
130 Arterial pressure cuff
131 Pulse oximetry probe
132 Pulse oximetry monitor
133 Electrocardiogram electrodes
134 Mechanical ventilator
135 Arterial line
136 Central venous line
137 Central venous blood oxygen saturation monitor
138 Electric syringe for inotropic agent venous infusion
139 Fluid bag
140 Perfusion pump for fluid administration
141 Venous line
142 Electric syringe for vasoactive and/or inotropic agent venous infusion

The invention claimed is:

1. A device for infusing at least two medicaments, comprising:
at least two actuators configured to cause the at least two medicaments to be infused;
at least one sensor configured to measure a value of at least two parameters; and
a controller configured to control the at least two actuators, wherein the controller is programmed to activate the at least two actuators based on the values of each of the at least two parameters and based on the dependency between the at least two medicaments,
wherein the controller includes a distance analyzer configured to determine a distance between a threshold value and a parameter position,
wherein the parameter position is defined by the values of the at least two parameters,
wherein the controller further includes a converting unit configured to convert the distance into a dose of one of the at least two medicaments, and
wherein the controller is programmed to activate at least one of the at least two actuators according to the dose.

2. The device as recited in claim 1, wherein the at least two parameters are selected from the group consisting of:
a systolic arterial pressure (SAP), a mean arterial pressure (MAP), a pulse oximetry plethysmographic waveform variation (POPV), a hemoglobin (Hb) concentration, a hematocrit (het), a heart rate (HR), a pulse pressure variation (PPV), a systolic pressure variation (SPV), a pre-ejection period variation (PEPV), a central venous blood oxygen saturation (ScVO2), and a stroke volume variation (SVV).

3. The device as recited in claim 1, wherein the at least one medicament is selected from the group consisting of: a fluid, red blood cells, a vasoactive agent, and a positively inotropic acting agent.

4. The device as recited in claim 1, wherein the controller further includes
a maximum device having a maxima memory containing a value for a maximum dose of the at least two medicaments,
a dose determining device configured to determine a dose of the at least two medicaments, and
a maximum stopper configured to stop the infusion of the at least two medicaments when the maximum dose is reached.

5. The device as recited in claim 1, wherein the controller further includes
an effect controlling device having an effect memory configured to store a list of the at least two medicaments and corresponding expected parameter changes,
a stopper configured to stop the infusion of a medicament, wherein the effect controlling device is programmed to activate the stopper if the at least two medicaments are infused and at least one corresponding expected parameter change does not occur.

6. The device as recited in claim 1, wherein the controller is a closed loop controller.

7. A method for infusing of at least two medicaments, the method comprising:
measuring at least two parameters;
determining a distance between a threshold value and a parameter position, wherein the parameter position is defined by values of the at least two parameters;
converting the distance into a dose of one of the at least two medicaments, activating at least one of at least two actuators according to the dose; and causing the at least two medicaments to be infused based on a value of each of the at least two parameters, and based on at least one dependency between the at least two medicaments.

8. The device as recited in claim 1, wherein the at least two parameters comprise a systolic arterial pressure (SAP).

9. The device as recited in claim 1, wherein the at least two parameters comprise a mean arterial pressure (MAP).

10. The device, as recited in claim 1, wherein the at least two parameters comprise a pulse oximetry plethysmographic waveform variation (POPV).

11. The device as recited in claim 1, wherein the at least two parameters comprise a hemoglobin (Hb) concentration.

12. The device as recited in claim 1, wherein the at least two parameters comprise a hematocrit (hct).

13. The device as recited in claim 1, wherein the at least two parameters comprise a heart rate (HR).

14. The device as recited in claim 1, wherein the at least two parameters comprise a pulse pressure variation (PPV).

15. The device as recited in claim 1, wherein the at least two parameters comprise a systolic pressure variation (SPV).

16. The device as recited in claim 1, wherein the at least two parameters comprise a pre-ejection period variation (PEPV).

17. The device as recited in claim 1, wherein the at least two parameters comprise a central venous blood oxygen saturation (ScVO2), a stroke volume variation (SVV), or an ScVO2 and an SVV.

18. The method as recited in claim 7, further comprising:
stopping an infusion of at least one of the at least two medicaments if the at least two medicaments are infused and at least one corresponding expected parameter change does not occur.

19. The method as recited in claim 7, wherein the measuring comprises measuring the at least two parameters with one sensor.

* * * * *